United States Patent [19]

DeLuccia, deceased et al.

[11] Patent Number: 4,502,482
[45] Date of Patent: Mar. 5, 1985

[54] ENDOTRACHEAL TUBE COMPLEX

[76] Inventors: Victor C. DeLuccia, deceased, late of Yonkers, N.Y.; Nancy DeLuccia, executrix, #116 Edgecliff Ter., Yonkers, N.Y. 10705; Ann Grincell, executrix, #315 W. 55th St., New York, N.Y. 10019; Henriette Kolodziejcuk, executrix, #1155 Warburton Ave., Yonkers, N.Y. 10701

[21] Appl. No.: 522,091

[22] Filed: Aug. 11, 1983

Related U.S. Application Data

[63] Continuation-in-part of Ser. No. 496,879, May 23, 1983.

[51] Int. Cl.³ .............................................. A61M 16/00
[52] U.S. Cl. ........................... 128/207.15; 128/207.14; 604/170; 604/119; 604/100; 604/165; 604/166
[58] Field of Search ...................... 128/207.14, 207.17; 604/170, 280, 119, 100, 165, 166

[56] References Cited

U.S. PATENT DOCUMENTS

| | | | |
|---|---|---|---|
| 3,087,493 | 4/1963 | Schossow | 128/207.15 |
| 3,407,817 | 10/1968 | Galleher, Jr. | 128/207.15 |
| 3,606,669 | 9/1971 | Kemble | 128/200.26 |
| 3,890,976 | 6/1975 | Bazell et al. | 604/280 |
| 3,937,220 | 2/1976 | Coyne | 604/119 |
| 4,027,659 | 6/1977 | Cami | 604/280 |
| 4,248,234 | 2/1981 | Assenza et al. | 604/170 |
| 4,248,235 | 2/1981 | Taylor | 604/100 |
| 4,289,128 | 9/1981 | Rusch | 128/207.15 |
| 4,340,046 | 7/1982 | Cox | 128/207.17 |
| 4,344,436 | 8/1982 | Kubota | 128/207.15 |

Primary Examiner—Henry J. Recla
Attorney, Agent, or Firm—Collard, Roe & Galgano

[57] ABSTRACT

An endotracheal complex for insertion into the trachea of a patient, and wherein the trachea branches through the carina trachea distally into two bronchi, includes a tube which has a distal blunt and atraumatically shaped tip so as to restrain passage of the tip beyond the carina tracheae into the bronchi and to serve as an internal palpator to identify an anatomical reference point, and an inflatable cuff near the tip for preventing any air or air component other than oxygen emanating from the source of oxygen to pass to the bronchi. A removable introducer is disposed in the tube and has a bevelled end portion to facilitate insertion of the tube through the larynx into the trachea. After the endotracheal tube is inserted into the trachea of a patient, the bevelled end portion is removed by pulling on the introducer tube or stylet. The bevelled end portion collapses off the blunt end of the endotracheal tube and can be pulled through the endotracheal tube to be removed and discarded. The remaining blunt end of the endotracheal tube, from which oxygen is fed to the patient, is so designed so that it will slip past the carina trachea into either bronchus of the patient. There is also provided a suction tube which fits into the endotracheal tube and which has a distinct curve at its distal end as it emerges from the blunt end of the endotracheal tube so that it can be easily directed to slide down the left or right bronchus of the patient in order to aspirate fluids from the lung.

27 Claims, 13 Drawing Figures

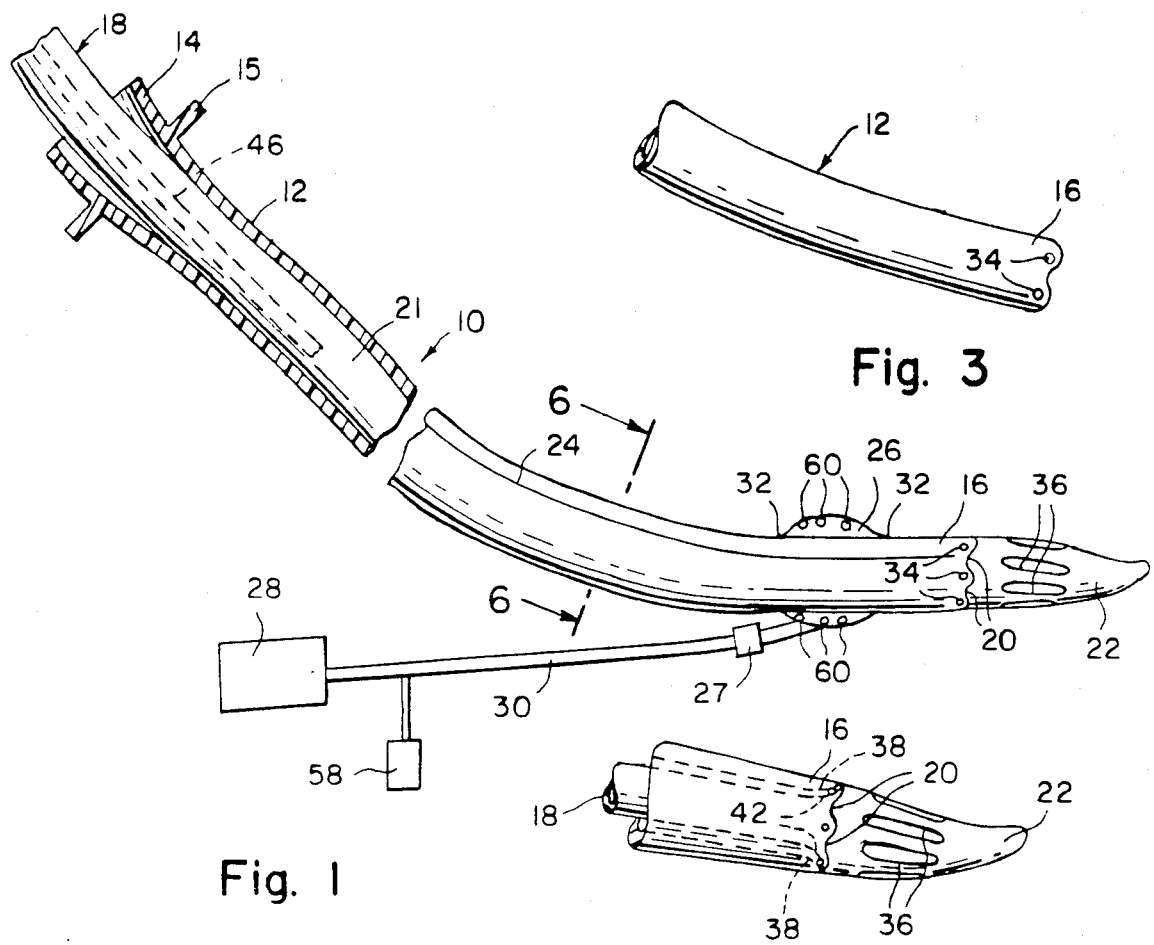
Fig. 3
Fig. 1
Fig. 2
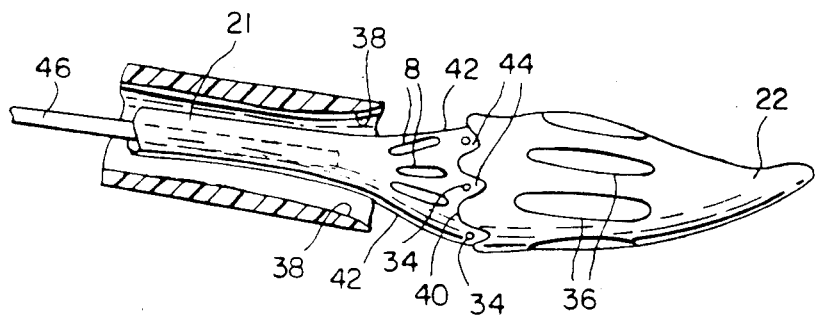
Fig. 4

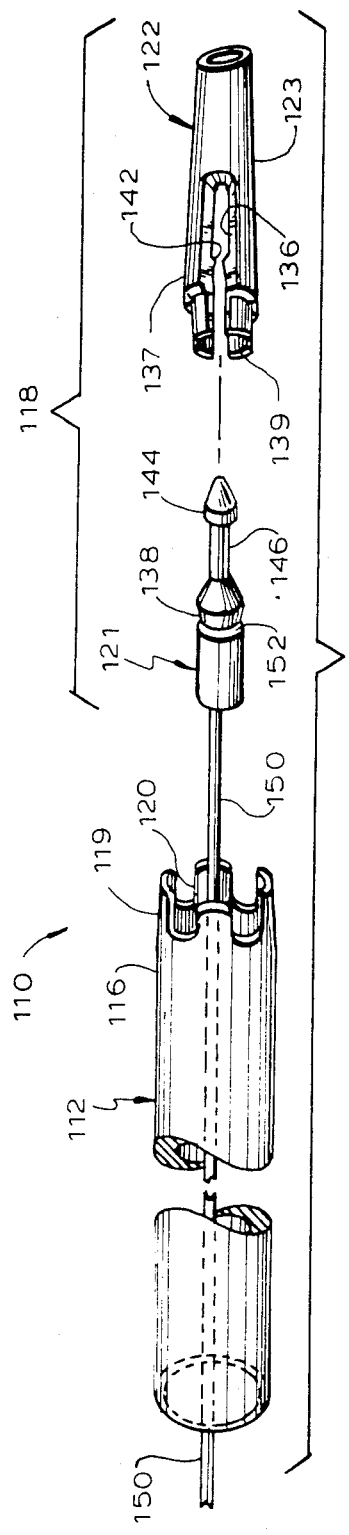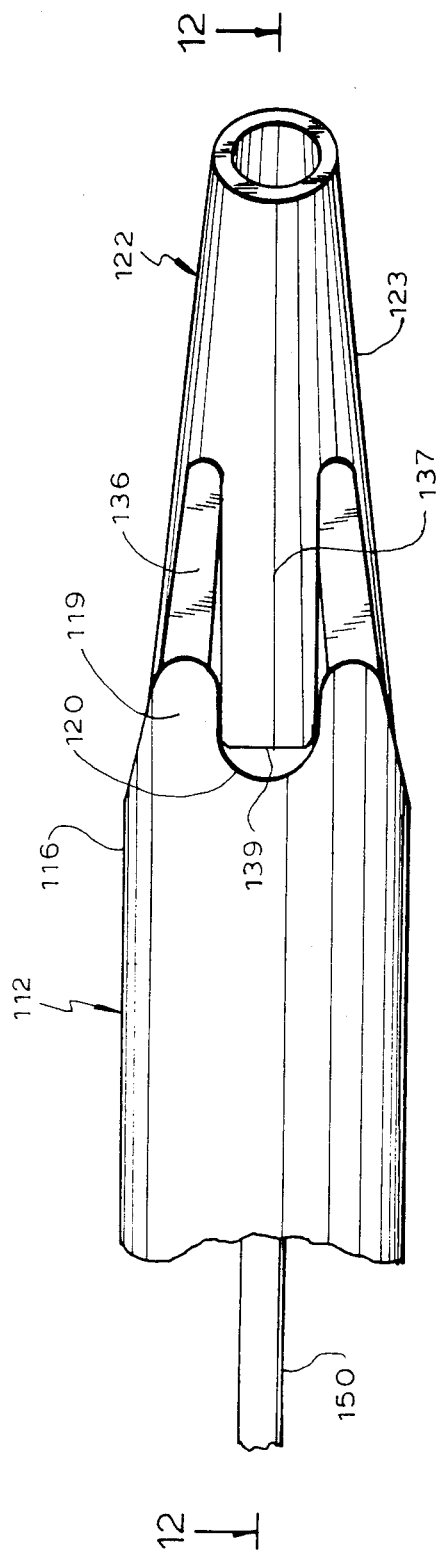

ENDOTRACHEAL TUBE COMPLEX

REFERENCE TO RELATED APPLICATIONS

This is a continuation-in-part application of my copending application, Ser. No. 496,879, filed May 23, 1983, entitled ENDOTRACHEAL TUBE COMPLEX.

BACKGROUND OF THE INVENTION

1. Field of the Invention

The invention relates to an endotracheal tube designed for accurate placement in the trachea in order to administrate oxygen or anesthetic gases, and to permit thorough cleansing of the lungs during the administration of endotracheal anesthesia or during its use with life supporting systems. It includes a distal inflatable cuff to effect an air seal in order to prevent the loss of oxygen during ventilation. It is mated with a removable introducer to facilitate atraumatic passage through the larynx. In another embodiment of the invention, a curved suction catheter is provided for insertion into the endotracheal tube and a means is provided for directing this catheter into either lung of the patient.

2. Description of the Prior Art

A number of endotracheal tubes are known. For an example the Lanz Controlled Pressure Cuff Endotracheal Tube consists of a plastic canulla, a permanently bonded, high-volume, low-pressure cuff, an inflation line, and a pressure-regulating valve. Once the cuff is inflated, the pressure-regulating valve will maintain a pressure range of 25 mm./Hg on the tracheal wall during expiration. The proximate end of the tube incorporates a 15 mm. adapter, which fits standard connectors on ventilators or anesthesia equipment. There are further known the argyle TARTAN TM I and TARTAN TM II endotracheal tubes. The TARTAN TM I tracheal tube is a high volume, low pressure cuffed endotracheal tube, which is optionally provided with a positive locking device. The TARTAN TM II tracheal tube is a low pressure cuffed endotracheal tube designed to seal the trachea with low endotracheal pressure, in most situations less than 25 mm. of Hg. There is further known the American TM tracheal tube with a radiopaque line and a single lumen. During anesthesia aspiration of foreign material from the lungs, utilizing suction catheters can be performed through the conventional endotracheal tubes. All of the aforesaid endotracheal tubes suffer from the disadvantage that their bevelled tip, once inside the trachea, becomes useless and actually poses a hazard, because it directs the endotracheal tube to one or the other of the main bronchi, and really facilitates entry into said bronchi, should the endotracheal tube migrate distally. Also, since most endotracheal tubes of the prior art are curved, the guiding tendency of the bevelled tip is enhanced by the curves of these prior art endotracheal tubes, which help to direct the tube towards one side or the other of the carina tracheae with distal motion. This is clearly an undesired effect, as only one lung may receive the benefit of ventilation and suctioning, and the contralateral lung none, causing it to obstruct and collapse.

There is also known an Argyle Touch-Trol TM Suction Catheter kit which is a transparent tube, the end of which is formed with two lateral lumens, and which has a proximate end which permits a limited amount of suction control. There is also known the Regu-Vac suction catheter made by Bard-Parker, Division of Becton, Dickinson & Co.

Straight suction catheters of the prior art have many disadvantages. One disadvantage is that only two or three distal openings are provided. These generally are not sufficient to remove most of the thick and copious tracheobronchial secretions in the short period of time that is needed to perform this function. Additionally, all of the distal openings or lumina can become easily plugged, so that the suction catheter will be rendered ineffective. In some instances, all but one of these distal openings can become occluded, so that the entire suction force is transmitted to one opening at the distal end of the suction tube. In such a situation, the resultant strong suction force will injure the bronchial mucosa, even if the suction is interrupted intermittently by the finger-tip control. Additionally, because of its straight direction, the catheter is usually aimed directly towards the main carina once it leaves the distal end of the endotracheal tube. The closer that the tip of the endotracheal tube is to the carina, the less the flexibility of the tip of the suction catheter, and the more traumatic it becomes to the main carina when it abuts against its wall before it is eventually diverted to one or the other main bronchi. Finally, the marked curve of the endotracheal tube of the prior art helps to direct the suction catheter towards the side the endotracheal tube is pointed, which, as has already been pointed out, is an undesired effect.

During the process of frequent suctioning in an intubated patient, the suction catheter may hit against the main carina most of the times it is inserted, and may thus traumatize the mucosa markedly. The injury becomes directly proportional to the number of insertions in which the catheter impinges on the main carina. Additionally, because of such anatomical factors as the direction of the right main bronchus, the suction catheter may enter only into the right main bronchus each time it is inserted. At best, the cleansing process with the suction catheters of the prior art is a "hit or miss" operation.

SUMMARY OF THE INVENTION

Accordingly, it is an object of the present invention to provide an endotracheal tube complex with a temporary bevelled tip for guidance during the insertion process only, and to remove that bevelled tip as soon as it has served its purpose, namely to facilitate the introduction of the endotracheal tube through the larynx into the trachea for the purpose of airway management in a patient.

It is another object of the invention to provide a suction tube for insertion into the endotracheal tube which can be directed into either lung of the patient and adequately remove the foreign material within the short period of time that is allotted for this maneuver.

In the invention, an endotracheal tube is provided with a removable inner introducer which is releasably locked therein to facilitate atraumatic passage of the mated complex through the larynx. At the end of the introducer is connected a bevelled tip so constructed as to releasably lock with the endotracheal tube, so angled for optimum entry into the larynx, and so structured to partially collapse for easy withdrawal. When the introducer is extracted, all that remains of the endotracheal tube complex is the endotracheal tube. This tube is shaped to lie naturally in the trachea and its tip is blunted to permit internal palpation of the main carina and to prevent easy entry into either lung should the tube migrate.

BRIEF DESCRIPTION OF THE DRAWINGS

Other objects and features of the present invention will become apparent from the following detailed description, considered in connection with the accompanying drawings which disclose the embodiments of the invention. It is to be understood, however, that the drawings are designed for the purpose of illustration only and not as a definition of the limits of the invention.

In the drawings, wherein similar reference characters denote similar elements throughout the several views:

FIG. 1 is a view, partly in cross section, of the endotracheal tube complex or catheter according to the invention showing its main component parts, namely the tube, the proximal end of the tube adapted to be connected to a supply of oxygen, the introducer, its bevelled tip, and the inflatable cuff mounted near a distal end of the tube;

FIG. 2 is an elevation view of a first embodiment of the introducer, showing the alignment of the bevelled end portion of the introducer with its atraumatically shaped tip removably coupled to the end of the tube;

FIG. 3 is a perspective view of the distal end portion of tube;

FIG. 4 corresponds to FIG. 2, but shows the bevelled tip of the introducer slightly withdrawn outwardly from the tube;

FIG. 10 is an exploded view of the distal end of another embodiment of the endotracheal tube complex or catheter according to the present invention;

FIG. 11 is a side elevational view of the distal end of the endotracheal tube complex of FIG. 10;

DESCRIPTION OF THE PREFERRED EMBODIMENTS

Figure 5:
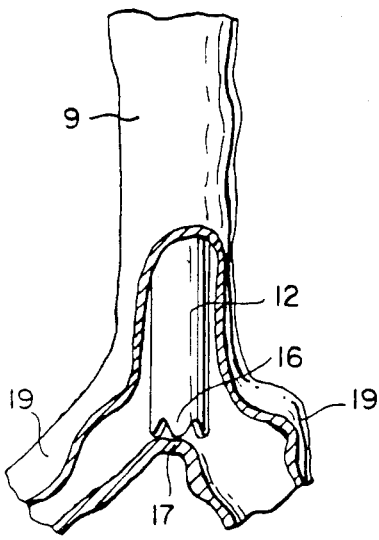
FIG. 5 is a perspective view of the trachea, partly opened, showing the tip of the tube just making contact with the carina tracheae.

Referring now to the drawings, and particularly to FIG. 1 thereof, there will be seen an endotracheal tube complex or catheter 10 for insertion into the trachea of a patient. Catheter 10 is made up of a tube 12 fitted with a flange 15 on its proximal end, and suitable for connection to a standard (non-illustrated) oxygen supply. For this purpose, tube 12 has a slightly flared proximal end 14.

Figure 6:
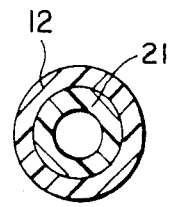
FIG. 6 is a cross-section along line 6—6 of FIG. 1.

Tube 12 is formed with a distal atraumatically shaped blunt tip 16, as shown in detail in FIG. 3, and includes an introducer 18 which is disposed in tube 12, as seen in FIGS. 1 and 6. Introducer 18 consists in this embodiment, of a tube portion 21 terminating at its distal end with a bevelled end portion 22 which normally extends outwardly from the tube 12. The bevelled end portion 22 permits tube 12 to be inserted through the patient's larynx into the trachea. Once tube 12 with introducer 18 is safely guided through the larynx into the trachea by means of bevelled end portion 22, end portion 22 is no longer required, having served its purpose. Thus, introducer 18 with its bevelled end portion 22 is withdrawn from the tube, to permit oxygen to be introduced in tube 12 to the patient.

Blunt tip 16 restrains tube 12 disposed in trachea 9 from passing beyond the carina tracheae 17 into one of the bronchi 19 of the patient as shown in FIG. 5. It is customary for tip 16 to be lifted slightly away from the carina trachea, once the tube 12 has been inserted. Blunt tip 16 is formed with a plurality of notches 20 which have completely smooth edges, while in contact with end portion 22. End portion 22 of introducer 18 complements the serrated edges or notches 20 formed in atraumatically shaped tip 16 when the endotracheal tube complex or catheter is slipped through the larynx, so that the combined tip 16 and bevelled end portion 22 of the introducer present a smooth atraumatic surface to the larynx and trachea.

Introducer 18 must meet two requirements. It must fit snugly into endotracheal tube 12, and the proximal end of end portion 22 must, during the insertion of the catheter into the larynx, fit tip 16 of tube 12 snugly. Moreover, once introducer 18 has fulfilled its function, and has guided endotracheal catheter 10 into the trachea, its end portion 22 must be so shaped, that it can be easily and quickly pulled outwards from tube 12. For this purpose, end portion 22 is bevelled and collapsible, and preferably slightly curved. It extends between 1 and 2 cm. from tip 16, and subtends an angle of between 35° and 45° with the axis of tube 12. End portion 22 engages notches 20 of tip 16 at the proximal end thereof. Thus, when introducer 18 is fully inserted into tube 12, bevelled end portion 22 projects distally outwards beyonds tip 16, so as to present together with tip 16 a substantially smooth external surface to the trachea of the patient.

Bevelled end portion 22 is designed to collapse and slide within tube 12, as introducer 18 is withdrawn. End portion 22 is therefore formed with a plurality of longitudinal slits 36 closed at each end, each slit having completely smooth edges. Tip 16 has an interior slanting portion 38, and bevelled end portion 22 has an exterior slanting portion 42 mating with the interior slanting portion 38, as shown in FIG. 4, so that introducer 18 can be smoothly withdrawn outwardly from tube 12, once the tube has been fully inserted into the trachea, and introducer 18 has therefore fulfilled its function. Introducer 18, adjacent to the locking mechanism may also include additional slits 8 to facilitate the collapse of the introducer upon withdrawal.

While it must be possible to easily pull the introducer 18 out from tube 12, the bevelled end portion 22 of the introducer must, at the same time, stay locked to tube 12, while endotracheal catheter 10 is slipped into the trachea of the patient. For this purpose there are provided locking means for releasably locking the introducer 18 to tube 12. This means that during insertion of introducer 18 into tube 12, when the introducer must remain locked to the tube, its bevelled end portion 22 must also remain in firm contact with the serrated edge of the atraumatically-shaped tip 16 of tube 12, which is formed with the aforedescribed notches 20. During insertion of endotracheal complex 10, the lock must effect a tight fit between the introducer 18 and endotracheal tube 12. The external surface of endotracheal tube 12 must remain smooth, and its diameter may not increase by the locking mechanism provided. Specifically the locking mechanism adapted must ensure that bevelled end portion 22, when in use, does not move longitudinally inwardly or outwardly with respect to tube 12, nor must it be allowed to turn or rotate within the tube. By smoothly mating the proximal or outwardly pointing edge portion 40 of bevelled tip 22 with notches 20 formed in tip 16, during proximal movement of endotracheal catheter 10 into the trachea of the patient, bevelled end portion 22 will either stay in place, when not encountering any resistance, or it will be pushed against tip 16 if any tracheal resistance, however slight, is encountered during such movement. Hence, tip 22 will not move further outwardly or in a distal direction during the inward inserting movement of endotracheal catheter 10.

After endotracheal catheter 10 has been fully introduced into the trachea of the patient, it becomes necessary to withdraw introducer 18 completely from the tube 12. For this purpose, as has already been stated, the bevelled end portion 22 is made collapsible. This is facilitated by the provision of slots 44 between respective slits 36. Each slot 44 has a length considerably smaller than the length of each slit 36, and is open at an end facing the tip 16 of the tube 12. In this manner an initial turning or twisting action will dislodge the mated serrated edge 40 from its normal mating contact with the notches 20. The tip 16 will, firstly, become unlocked from the bevelled edge 22, and thereafter the introducer 18 can be easily pulled out by exerting a pulling action or tug on the proximal end thereof, so that it is easily and safely withdrawn from the tube 12. In this manner the primary object of the invention has been achieved by the atraumatically-shaped tip 16 coming to rest temporarily against the carina trachea 17 without any risk of tip 16 being introduced into one or the other bronchi 19 of the patient. Notches 20 formed in tip 16 have completely smooth and rounded edges, so as to be completely atraumatic and prevent damage whenever they impinge on the carina tracheae. For this purpose it is best if notches 20 are substantially evenly distributed over the periphery of tip 16. It has been found in practice that the optimum number of notches 20 equals four, and that the depth of each notch is optimum at about four mm. The tube should be appropriately marked, and preferably be color coded; centimeter marks should denote the length of the tube. The tube 12 is preferably slightly curved initially, and preferably made of semi-rigid plastic, non-toxic, non-allergic material capable of resisting corrosion and deterioration from chemicals, gas sterilization and autoclaving. It is also preferably of sufficient rigidity to maintain the shape thereof when inserted for a period of several days into the trachea. It must not kink or swell during operative use. Furthermore tube 12 must have a durometer hardness sufficient to resist kinking, so that no critical reduction in the cross-section of it occurs when it is bent. The material from which tube 12 is made may be metal covered by a latex or rubber sheet, rubber or latex into which a coiled wire or heavy silk is incorporated, neoprene or compounds thereof, latex with a continuous monofilament embedded therein, or synthetic plastic material, such as a polymer including a primary plasticizer and a stabilizer. The polymer may consist of polyvinyl and polyethylene, and the primary plasticizer may be tributyl acetyl or dialkyl phtalatate sebacate; the stabilizer preferrably includes organotonin.

In its first embodiment, introducer 18 itself should be made of semi-rigid plastic material similar to, but slightly softer than the tube material. It must be adapted to receive a thin shaping stylet 46 (as shown in FIG. 4) when tube 12 and introducer 18 are operatively emplaced in the trachea of a patient, so that shaping stylet 46 can be used to reshape, if necessary, the curvature of tube 12, and of introducer 18 emplaced in the tube. The surface of tube 12 and the surface of introducer 18 facing the trachea and bronchi must have a mirror-smooth finish.

Figure 9:
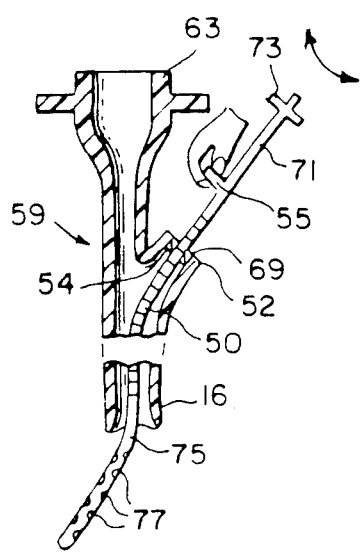
FIG. 9 corresponds to FIG. 7, but with the suction catheter rotated by 180°, showing the effect on the distal curved end of the suction catheter.
Figure 7:
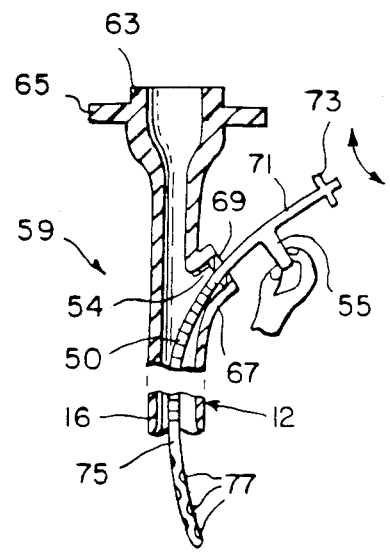
FIG. 7 is a longitudinal cross-section of an adapter permitting manipulatable fingertip suction control of a suction catheter insertable into the adapter fitted into the proximal end of the endotracheal tube after withdrawal of the introducer, and protruding beyond the tip of the tube, so as to control suction from a lung, and yet permit oxygen supply.
Figure 12:
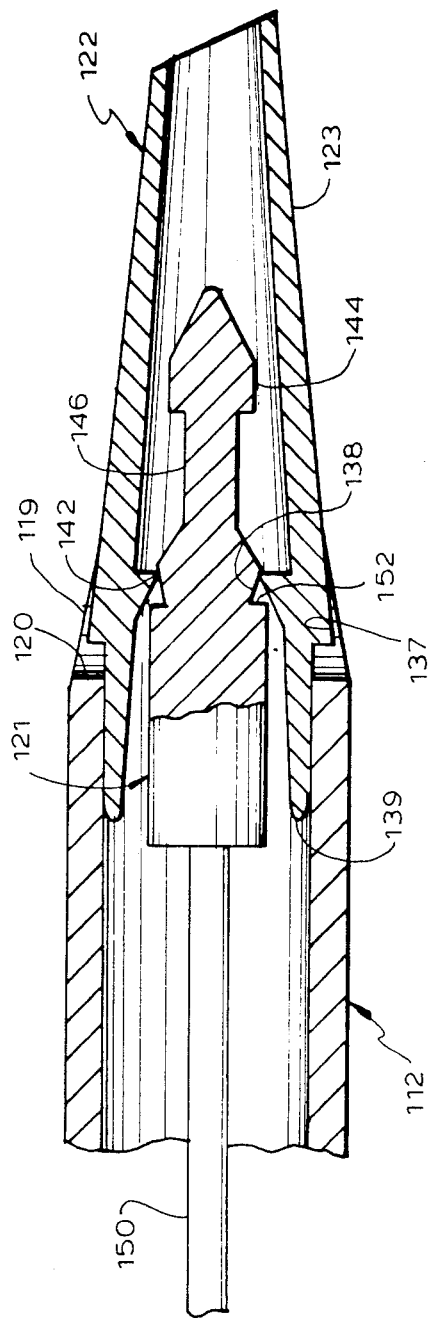
FIG. 12 is a cross-sectional view of the endotracheal tube complex of FIG. 11 taken along the line 12—12 of FIG. 11.
Figure 13:
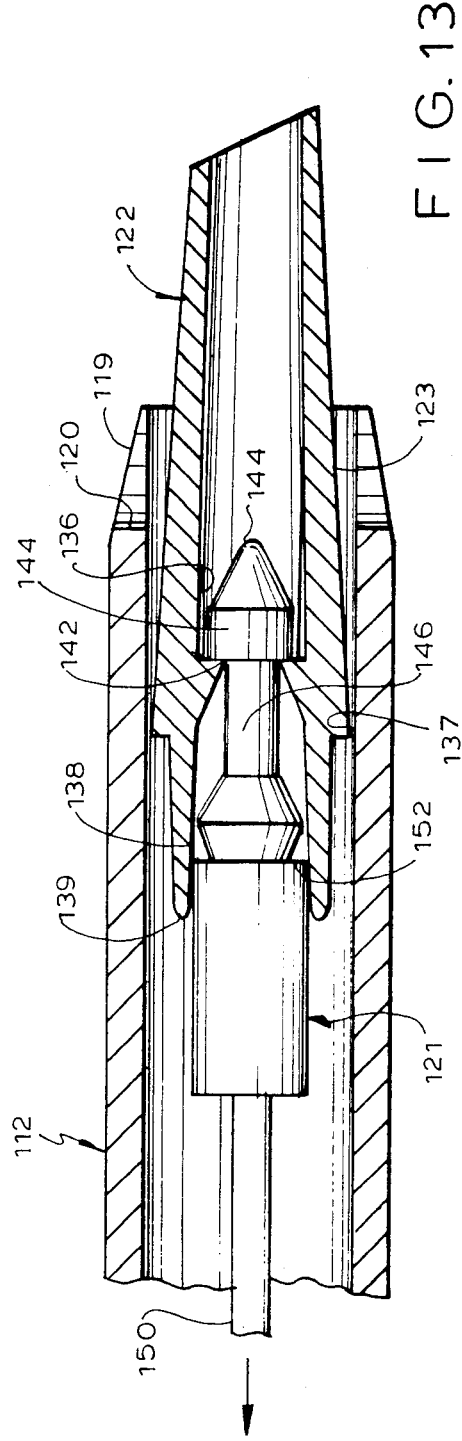
FIG. 13 is a view of the distal end of the endotracheal tube complex similar to the view of FIG. 12 showing the end portion of the inserter collapsed and partly withdrawn.

Following introduction of tube 12 into the trachea of the patient, in addition to furnishing oxygen to the patient, it may additionally also be necessary to intermittently withdraw fluid from the lungs of the patient. For this purpose, as best seen in FIG. 7, there is inserted an adapter 59 into the proximal end of tube 12 which permits selectable control of the degreee of suction applied to the lungs of a patient. A connecting portion 63 of the adapter 59 serves to be connected to the (non-illustrated) oxygen supply. A branch 67 branches off from adapter 59, and is formed with an inlet 54. Inlet 54 is fitted with a penetrable air seal 69. Fluid aspirating means, for example a suction catheter 71 of an outer diameter smaller than that of the inner diameters of adapter 59 and tube 12 is connected with its proximal end 73 to a suction generating means (not-illustrated). Catheter 71 is inserted through seal 69 and into tube 12 to extend beyond tip 16. Its distal end 75 is formed with a plurality of lumina or openings 77. The length of suction catheter 71 is such that it can be passed into one of the bronchi of the patient. Suction is only applied intermittently to the proximal end 73 of suction tube 71. This is accomplished by a branch 55 branching off from the suction catheter 71 having a normally open end. Only when the open end is closed by fingertip control is suction effective. Otherwise a vacuum or partial vacuum cannot be maintained within catheter 71, as atmospheric pressure then prevails within the interior of catheter 71, namely when the branch 55 is open. The intermittent suction applied does not interfere with the normal supply of oxygen to the patient through tube 12. The longitudinal suction catheter 71 is advantageously curved gently within 2 cm. to 5 cm. from its distal end 75, so that it can be directed away from the main carina, and towards one lung or the other by rotation thereof about its axis. For this purpose there is provided an indicator in the form of a dial 52, indicating the degree of rotation of the suction catheter 71 by the position of the fingertip manipulatable control means in the form of the branch 55, and consequently the position of its distal end 75, when the suction catheter 71 is rotated within the air seal 69. It will thus be seen from a comparison of FIGS. 7 and 9, that the distal end of suction catheter 71 with its lumina 77 can be directed to selectively suction one lung or the other. The suction catheter 71 is preferably transparent and calibrated along its longitudinal direction with visible distance markers, so that its depth of insertion can be observed through the transparent tube 12. The suction catheter 71 should be made of a material sufficiently rigid to maintain its directional tendency, and strong enough to resist any change in its inside diameter, in the event it is bent. Its walls should not collapse inwardly when a suction force nearly equalling a vacuum is applied along the interior of the suction catheter. Catheter 71 must additionally also be sufficiently non-flexible, so that its distal end cannot be tied into a knot. In order to effect aspiration of fluid from the patient effectively, and as best seen in FIG. 7, a distal end of the suction catheter 71 having a length up to about 6 cm. from the tip 16 of tube 12, and a diameter between 3 mm. and 4 mm., as has already been stated, is formed with up to about six lumina or openings 77 distributed evenly about its periphery. Each lumen or opening is about 2 mm. wide and has a length of about 5 mm.

Figure 8:
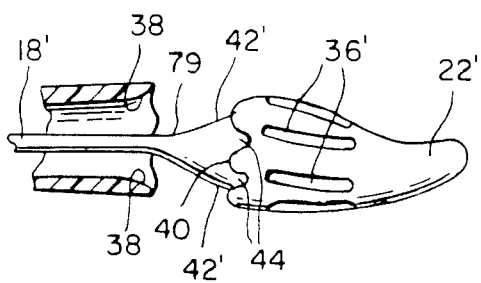
FIG. 8 is an elevation view of a second embodiment of the introducer in the form of a stylet to which a bevelled end portion is attached.

An alternate embodiment of an introducer 18' is shown in FIG. 8. This embodiment is used when it is not necessary, or not desired to administer oxygen while the introducer 18' is being inserted. Here the stem of the introducer is implemented as a flexible stylet, for example a malleable metal stylet 79 preferably bonded to the bevelled end portion 22'. Otherwise the bevelled end portion 22', slits 36', and slits 44' correspond to the bevelled end portion 22, slits 36, and slits 44, respectively, of the embodiment shown in FIGS. 2 and 4. The embodiment of the introducer shown in FIG. 8 is much simpler and easier to use, because the insertion of the introducer 18' is accomplished very quickly and in a less complicated manner. The locking mechanism remains essentially unchanged from that used in the embodiments shown in FIGS. 2 and 4, and the larynx of the patient is protected in the manner already described during insertion of this second embodiment of introducer 18' with its associated endotracheal catheter.

In the embodiment shown in FIGS. 10 to 13 there is shown an endotracheal tube complex 110 comprising a tube 112 and an introducer 118. Endotracheal tube complex 110 performs the same functions and operates in a manner similar to that of the above described endotracheal tube complex 10. Tube 112 is configured similarly to tube 12 of endotracheal tube complex 10 having a distal atraumatically shaped blunt tip 116 provided with notches 120 at the end thereof defining forward extending projections 119 therebetween.

As clearly seen in FIG. 10, introducer 118 comprises a frustro-conically shaped bevelled end portion 122 and an actuator 121. Bevelled end portion 122 is basically tubular shaped and is provided with a skirt portion 123 having slits 136 therein which open to the rear of skirt portion 123 to define rearwardly extending projections 137 therebetween. The ends of projections 137 are provided with stepped-down extensions 139 whose surfaces are below the surfaces of projections 137. In the expanded or non-collapsed condition of bevelled end portion 122, which will hereinafter be explained and described, projections 137 are aligned with notches 120 so that projections 119 extend into slits 136 while projections 137 extend into and are engaged with notches 120 in the end of tip 116 of tube 112. When bevelled end portion 122 is so positioned in tip 116 of tube 112, extensions 139 lie within tube 112, as clearly seen in FIGS. 11 and 12, to maintain the alignment thereof.

Actuator 121 serves to maintain bevelled end portion 122 in an expanded condition until it is desired to collapse end portion 122. Thus, actuator 121 comprises an elongated member provided with an annular cam surface 138 which engages with inwardly directed protuberances 142 which are interiorly positioned on projections 137 of bevelled end portion 122. When protuberances 142 are thus engaged with cam surface 138, projections 137 are expanded outwardly so as to engage notches 120 of tube 112 as described above. In this condition endotracheal tube complex 110 may be easily and atraumatically inserted into a patient's trachea. Forwardly of cam surface 138 there is provided an annular undercut portion 146 on actuator 121 which terminates in a radially outwardly extending annular step 144. A filament, designated 150, is operatively connected to the rearmost end portion of actuator 121 and extends through the length of tube 112 so as to be grasped at the free end thereof. Thus, when it is desired to withdraw introducer 118 from tube 112, a pulling force is exerted on the free end of filament 150 which causes actuator 121 to move rearwardly with respect to bevelled end portion 122 thereby disengaging protuberances 142 from cam surface 138. As a result of the disengagement of cam surface 138 from protuberances 142, projections 137 collapse sufficiently to permit bevelled end portion 122 to fit within tube 112 and to allow step 144 to engage protuberances 142, as actuator 121 is further withdrawn. The continued exertion of a pulling force on filament 150 which is transferred, because of the engagement of step 144 with protuberances 142, to a like force on bevelled end portion 122 results in the withdrawal of end portion 122 from tube 112, as clearly seen in FIG. 13.

A raised annular step, designated 152, on actuator 121 at the rear of cam surface 138 prevents the further insertion of actuator 121 into bevelled end portion 122 beyond that needed to expand projections 137. Filament 150 may be any suitable filament including such as used in connection with endotracheal tube complex 10.

As with all endotracheal tubes, an inflatable cuff 26 is provided near end 16 of tube 12, as clearly seen in FIG. 1. It is desirable that inflatable cuff 26 be neither underinflated nor overinflated. For this purpose, since it is known at what pressure the cuff is correctly inflated, it is possible to insert a pressure sensor 58 into auxilliary tube 30 connecting air pressure generating means 28 with inflatable cuff 26. The length of cuff 26 is preferably between 2 cm. and 4.5 cm., and its distal end is preferably spaced at most 2 cm., preferably 1 to 1.25 cm. proximally from the tip 16 of tube 12. Cuff 26 is capable of holding a volume of air between about 2 milliliters to about 6 milliliters, and it has an effective air seal between 15 mm. to about 30 mm. of mercury effected by a substantially leak-proof two-way air valve 27 inserted into tube 30. This air valve will limit the maximum air pressure which can be transmitted to cuff 26, and will also act as a release valve, should the air pressure within cuff 26 exceed a certain predetermined value. Inflatable cuff 26 located near the distal end of tube 12, is made of an elastic material which is distended by air until the resultant balloon seals the air passages. It may be made of latex, rubber, or Penrose drain. Cuffs may be made in either single or double wall construction. The double wall construction may be a bulge (Guedel) type, or a flat (Waters) type. The inflatable cuff is preferably bonded into the tube itself. A proper inflatable cuff is able to expand to 1½ times of the external diameter of the endotracheal tube. When cuff 26 is inflated, the inferior edge of the balloon should be approximately 2 cm. from the edge or tip 16 of endotracheal tube 12.

OPERATION

The straight distal end of the endotracheal tube is long enough to first palpate the main carina and then to lie straight in the trachea, parallel to its sides, after the tube has been withdrawn 3 cm. to 5 cm. from the main carina. This is the significant improvement offered by the endotracheal tube according to the present invention. It can be placed at a target site which is localized by internal palpation and impingement. Accordingly, the correct placement of the endotracheal tube is ensured by finding fixed points in the trachea after the introducer is removed.

This placement is accomplished as follows: After palpating the main carina of the trachea with the specially shaped tip of the endotracheal tube, the first anatomical reference point is established. The endotracheal tube is then withdrawn 3 cm. to 5 cm. from the first anatomical reference point, and the second and final placement point is now established. This final placement point of the endotracheal tube in the trachea is marked for future reference by correlating it with another fixed external anatomical site, such as the upper gingival border with the head in the neutral position. This identification always becomes a quick check point whenever the location of the endotracheal tube in the trachea is questioned.

The configuration of the endotracheal tube according to the present invention differs from that of the prior art. This distal portion is straight so that it lies in the trachea parallel to its walls and does not point towards one side or the other. The proximal portion is curved so that it can protrude naturally from the larynx to the lips. In contrast thereto, the sweeping curve of the endotracheal tube of the prior art may, of itself, cause the tube to lie curved in a straight tubular structure (trachea) and direct the distal portion of the tube toward one or the other lung should the tube be inserted deeper. This same curve may also serve to obstruct the lumen of the bevelled tip by impinging against the wall. As the average distance from the vocal cords to the main carina in males is 12 cm. to 14 cm., and in females is 10 cm. to 14 cm., because of the stated measurements, and to correct the above-described curve of the prior art, the distal end of the present endotracheal tube is straight and approximately 15 cm. in length. Because the average distance from the lips to the vocal cords in males is 12 cm. to 16 cm., and in females is 10 cm. to 14 cm., the proximal curved portion of the endotracheal tube is approximately 21 cm. in length, of which 16 cm. is needed to clear the distance from the vocal cords to the lips and 5 cm. to allow sufficient protrusion of the tube from the mouth. The length of the entire endotracheal tube, in all, is about 36 cm.

The straight distal end of the endotracheal tube may pose a problem at the beginning for those physicians accustomed to using only a curved tube. This problem, however, is more apparent than real, since a straight and rigid tube which is 40 cm. long and 8 mm. wide (Jackson bronchoscope) can be passed with ease directly into the larynx without even the use of a laryngoscope. Its direct passage is accomplished in 98% of the patients, regardless of the prominence of the teeth, neck size, build, depth of the epiglottis, and the like. A good laryngoscopic exposure of the larynx is all that is necessary to pass the present endotracheal tube complex through the trachea.

Should a curve of higher curvature become absolutely necessary for the introduction of the endotracheal tube complex because of unusual circumstances, a thin stylet can be passed through the introducer and curved to a desired arc. It is always best to pass an endotracheal tube complex through the trachea when it has been very well lubricated, especially at the locking mechanism and tip, and, if possible, without the use of my stylet. A well-constructed cuff 2 cm. 4.5 cm. long is approximately 100% effective in preventing aspiration into the lung, and in forming an airtight seal for pressure ranges emanating from the lung within 20 mm. to 30 mm. of mercury is available. The volume of air that is needed to inflate the cuff is usually 2 ml. to 6 ml. The larger the tube, the less the amount of air is needed to occlude the trachea. If the cuffs are inflated ad terminum, the inter-cuff pressure rises to a peak until the cuff balloons out at its weakest point. Further addition of air then causes a fall in the intracuff pressure. This usually occurs after 8 ml. to 12 ml. of air is pumped into the cuff. The cuff ruptures only when much larger volumes of air (up to 40 ml.) are used and frequently instilled at a rapid rate. The cuff must be positioned 1.0 cm. to 1.25 cm. from the distal end of the tube in order to prevent herniation of the inflated cuff into the lumen of the endotracheal tube.

Most of the pressure exerted in order to inflate the conventional endotracheal tube cuff up to the point where it becomes an effective airway seal at 15 mm. to 20 mm. of mercury is needed to overcome the elasticity of the rubber. A small portion of this end point pressure is exerted laterally on the trachea, usually between 10 ml. to 15 ml. of mercury (which then approximates the mean capillary blood pressure in the trachea).

The endotracheal tube and the introducer are required to be sterile, and consequently the endotracheal complex of the present invention is preferably made as a disposable unit in a sterile package. Also, the endotracheal catheter must be available in various dimensions to fit into the trachea of children and adults, men and women. For this purpose, the tube will be supplied in sizes where its external diameter varies from 4.5 mm. to 14 mm. Its internal diameter will correspondingly have sizes varying from 4 mm. to 12 mm. The introducer should slide easily within the endotracheal tube. The external diameter of the introducer will be supplied in sizes from 3.5 mm. to 13 mm., and have corresponding respective internal diameters ranging from 3 mm. to 12 mm. Its length is preferably 3-4 cm. greater than the length of the corresponding endotracheal tube used in conjunction therewith, so that its length ranges from 13 cm. to 40 cm.

So as to make the location of the endotracheal tube more easily pictured on X-ray examination, a thread 24 substantially radiopaque throughout its length is provided, and is best incorporated into the wall of the tube 12, as clearly seen in FIG. 1.

When the endotracheal catheter 10 or 110 is in place in the trachea, in order to prevent the loss of any air or air component other than oxygen emanating from an oxygen source, there is provided an inflatable cuff 26 near its tip 16, as clearly seen in FIG. 1, which is inflated by conventional air pressure generating means 28 connected through an auxilliary tube 30 to the inflatable cuff 26. Thread 24 will normally extend up to tip 16, and will be radiopaque throughout its length, except for portions 32 thereof which are not radiopaque, and are located on either side of inflatable cuff 26. This interruption of the radiopaque thread will disclose the position of cuff 26 in relation to the cervical vertebrae, and thus indirectly relate its position to the larynx, which cuff 26 must not injure by impinging therewith. Also radiopaque beads or elements 34 are incorporated into the wall of tube 12 between adjacent notches 20 and near distal projections of tip 16, so that an X-ray examination can show the alignment of elements 34, evaluate the alignment of the trachea, X-ray tube and the X-ray plate, and disclose the location of tip 16 in relation to the carina tracheae.

Certain requirements are imposed on introducer 18. Thus, it will be appreciated that, as it may be necessary to administer oxygen through the endotracheal catheter, even when introducer 18 is introduced with its associated tube 12 into the trachea of the patient, introducer 18 is capable of being fitted to any standard connector for the administration of oxygen. It will normally protrude between 3 cm. to 4 cm. from the proximal end of the endotracheal tube 12, so that it can be easily grasped and pulled out. Introducer 18 should have an external diameter as large as possible to match the internal diameter of the endotracheal tube that it is used with. This diameter should however be small enough to allow the introducer to be easily pulled out of the endotracheal tube that it serves.

While several embodiments of the present invention have been shown and described, it will be obvious to those persons of ordinary skill in the art, that many changes and modifications may be made thereunto, without departing from the spirit and scope of the invention.

What is claimed is:

1. An endotracheal tube complex for insertion into the trachea of a patient, and wherein the trachea branches through the carina tracheae distally into two bronchi, said endotracheal complex having a proximal end for connection to a source of oxygen, comprising in combination a tube having a blunt and atraumatically shaped distal tip so as to restrain passage of said tip beyond the carina tracheae into the bronchi, and to establish an anatomical reference point by internal palpation, said tube including a plurality of projections formed on the distal tip thereof and defining a plurality of notches therebetween, an inflatable cuff disposed on said tube adjacent to said tip for closing off the space between the periphery of said tube and the trachea of the patient, thereby preventing any air or air component other than oxygen emanating from said source of oxygen to pass to the bronchi, a removable introducer disposed in said tube having a bevelled end portion extending from the distal tip of said tube so as to form a smooth atraumatic connection therewith, to facilitate insertion of said tube through the larynx into the trachea, said bevelled end portion of said introducer having on its proximal side a plurality of projections substantially mating with said notches at the distal tip of said tube, so as to engage said bevelled end portion to said blunt tip of said endotracheal tube, said introducer including a filament having a length greater than said tube and extending therethrough so that said introducer may be removed from said tube by the withdrawal thereof, and means for releasing the engagement of said bevelled end portion to the distal tip of said tube to permit removal of said introducer from said tube.

2. The endotracheal complex as claimed in claim 1, wherein said notches are substantially evenly distributed over the periphery of said tip.

3. The endotracheal complex as claimed in claim 2, wherein said number of notches equals four.

4. The endotracheal complex as claimed in claim 1, wherein said means for releasing the engagement of said bevelled end portion to the distal tip of said tube includes said tip having an interior slanting portion, and said bevelled end portion having an exterior slanting portion mating with said interior slanting portion, being collapsible, and formed with a plurality of longitudinal slits disposed around its periphery closed at each end, each slit having completely smooth edges, whereby the bevelled end portion of said introducer can be disengaged from the distal tip of said tube and said introducer withdrawn from said tube once said tube has been inserted into the trachea.

5. The endotracheal complex as claimed in claim 4, additionally comprising further slits disposed on the end of said introducer adjacent to said bevelled end portion.

6. The endotracheal complex as claimed in claim 1, further comprising a radiopaque element incorporated into the wall of the tube between adjacent notches and near distal projections of said tip, whereby an X-ray examination can disclose the location of said tip in relation to said carina tracheae and determine the alignment between X-ray tube, trachea and X-ray plate.

7. The endotracheal complex as claimed in claim 1, further comprising a thread disposed within said tube which is radiopaque throughout its length except in small portions thereof bordering each end of said cuff, whereby an X-ray examination can disclose the position of said tube within the trachea, and the position of said cuff in relation to the cervical vertebrae.

8. The endotracheal complex as claimed in claim 1, wherein said filament of said introducer includes a flexible and thin guiding stylet having an outside diameter substantially smaller than the inside diameter of said tube, said bevelled end portion being secured to a distal end of said guiding stylet.

9. The endotracheal complex as claimed in claim 8, wherein said guiding stylet is made of a malleable metal.

10. The endotracheal complex as claimed in claim 1, wherein said introducer fits smoothly into said tube and wherein sid bevelled end portion has a substantially frusto-conically shaped portion projecting distally about 1–2 centimeters from the distal end of said tip, and a terminal portion extending about 1 centimeter from the distal end of said frustro-conically shaped portion, said tip and said bevelled end portion substantially presenting a smooth external surface to the trachea.

11. The endotracheal complex as claimed in claim 10, wherein said introducer has a longitudinal axis, and wherein said terminal portion subtends an angle between 35° to 45° with said axis.

12. The endotracheal complex as claimed in claim 1, additionally comprising a suction catheter insertable into said endotracheal tube to exit from said endotracheal tube tip subsequent to the removal of said removable introducer, said suction catheter being curved at its distal end, and guide means formed on the proximal end of said suction catheter for directing said suction catheter into one or the other bronchus of the patient.

13. The endotracheal complex as claimed in claim 12, wherein said guide means comprises an indicator coupled to said suction catheter for defining the orientation of the distal end of said suction catheter.

14. The endotracheal complex as claimed in claim 12, wherein said suction catheter includes fingertip manipulatable control means for regulating the amount of suction applied to the proximal end of said suction catheter.

15. The endotracheal complex as claimed in claim 12, wherein said suction catheter includes a plurality of lumena disposed on the periphery of said catheter adjacent to its distal end.

16. The endotracheal complex as claimed in claim 1, further including signaling means providing a signal when said cuff is underinflated or overinflated.

17. The endotracheal complex as claimed in claim 16, further comprising a pressure tube connected to said cuff, and wherein said signaling means includes a pressure sensor located in said pressure tube.

18. The endotracheal complex as claimed in claim 1, wherein said cuff is bonded onto said tube.

19. The endotracheal complex as defined in claim 1, wherein said bevelled end portion includes a skirt portion having slits therein defining said projections therebetween.

20. The endotracheal complex as defined in claim 19, wherein said means for releasing the engagement of said bevelled end portion to the distal tip of said tube includes means for inwardly collapsing the skirt portion of said bevelled end portion to thereby disengage the projections thereof from said notches on the distal tip of said tube.

21. The endotracheal complex as defined in claim 20, wherein said means for inwardly collapsing the skirt portion of said bevelled end portion includes inwardly directed protuberances protruding from the projections of said end portion, an actuator having an annular cam surface thereon disposed interiorly in said end portion and moveable between a first position wherein the annular cam surface engages the inwardly directed protuberances to expand said skirt portion outwardly so that said projections and said notches on the distal tip of said tube are aligningly engaged, and a second position where said cam surface is disengaged from said protuberances and said skirt is thus allowed to relax and collapse inwardly.

22. The endotracheal complex as defined in claim 21, wherein said actuator further includes a rearwardly facing annular step which abuttingly engages with said inwardly directed protuberances when said actuator is in said second position.

23. The endotracheal complex as defined in claim 22, wherein said filament is attached to said actuator so that the exertion of pulling force on said filament moves said actuator from said first position to said second position and the continued exertion of such force on said filament withdraws said introducer from said tube because of the abutting engagement of said actuator step and said protuberances.

24. The endotracheal complex as defined in claim 19, wherein the projections of said bevelled end portion include stepped-down extensions which engage the inside wall of said tube when said projections are engaged in said notches of said tube to thereby align said bevelled end portion with said tube and prevent a dislocation thereof.

25. The endotracheal complex as defined in claim 1, wherein said filament includes a hollow tube having an external diameter smaller than the internal diameter of said endotracheal tube, said bevelled end portion being connected to said introducer tube having at least one opening so that oxygen, connected to the proxal end of said introducer tube will pass out of said at least one opening of said bevelled end portion.

26. A method of introducing an endotracheal tube into the trachea of a patient, comprising:
  (a) introducing an endotracheal tube complex atraumatically into the trachea of a patient, said endotracheal tube complex including
    a tube having a blunt and atraumatically shaped distal tip so as to restrain passage of said tip beyond the carina tracheae into the bronchi, and to establish an anatomical reference point by internal palpation, said tube including a plurality of projections formed on the distal tip thereof and defining a plurality of notches therebetween,
    an inflatable cuff disposed on said tube adjacent to said tip for closing off the space between the periphery of said tube and the trachea of the patient, thereby preventing any air or air component other than oxygen emanating from said source of oxygen to pass to the bronchi,
    a removable introducer disposed in said tube having a bevelled end portion extending from the distal tip of said tube so as to form a smooth atraumatic connection therewith, to facilitate insertion of said tube through the larynx into the trachea, said bevelled end portion of said introducer having on its proximal side a plurality of projections substantially mating with said notches at the distal tip of said tube, so as to engage said bevelled end portion to said blunt tip of said endotracheal tube, said introducer including a filament having a length greater than said tube and extending therethrough so that said introducer may be removed from said tube by the withdrawal thereof, and
    means for releasing the engagement of said bevelled end portion to the distal tip of said tube to permit removal of said introducer from said tube,
  (b) removing the removable introducer from said endotracheal tube,
  (c) palpating the main carina of the trachea with the distal tip of said endotracheal tube thereby establishing an anatomical reference point for said tube, and
  (d) withdrawing said endotracheal tube 3 to 5 centimeters from said anatomical reference point to a final placement point.

27. The method of introducing an endotracheal tube into the trachea of a patient as defined in claim 26, wherein the distal portion of said endotracheal tube is substantially straight so as to lie in the trachea parallel to the walls thereof.

* * * * *